United States Patent
Nambiar et al.

(10) Patent No.: US 10,738,266 B2
(45) Date of Patent: Aug. 11, 2020

(54) STRUCTURED LIQUID COMPOSITIONS COMPRISING COLLOIDAL DISPERSIONS OF POLY ALPHA-1,3-GLUCAN

(71) Applicant: DuPont Industrial Biosciences USA, LLC, Wilmington, DE (US)

(72) Inventors: Rakesh Nambiar, West Chester, PA (US); Jayme L. Paullin, Exton, PA (US); Ji Yeon Huh, Newark, DE (US); Natnael Behabtu, Wilmington, DE (US)

(73) Assignee: DUPONT INDUSTRIAL BIOSCIENCES USA, LLC, Wilmington, DE (US)

( * ) Notice: Subject to any disclaimer, the term of this patent is extended or adjusted under 35 U.S.C. 154(b) by 0 days.

(21) Appl. No.: 15/572,223

(22) PCT Filed: May 19, 2016

(86) PCT No.: PCT/US2016/033245
§ 371 (c)(1),
(2) Date: Nov. 7, 2017

(87) PCT Pub. No.: WO2016/196021
PCT Pub. Date: Dec. 8, 2016

(65) Prior Publication Data
US 2018/0127682 A1 May 10, 2018

Related U.S. Application Data

(60) Provisional application No. 62/169,134, filed on Jun. 1, 2015, provisional application No. 62/169,118, filed on Jun. 1, 2015, provisional application No. 62/169,103, filed on Jun. 1, 2015.

(51) Int. Cl.
| | | |
|---|---|---|
| C11D 1/00 | (2006.01) |
| C11D 3/22 | (2006.01) |
| C11D 3/386 | (2006.01) |
| C11D 3/37 | (2006.01) |
| B08B 3/04 | (2006.01) |
| A61K 8/04 | (2006.01) |
| A61K 8/73 | (2006.01) |
| A61Q 5/02 | (2006.01) |
| A61Q 19/10 | (2006.01) |
| C08B 37/00 | (2006.01) |
| C11D 3/00 | (2006.01) |
| C11D 17/00 | (2006.01) |
| A61Q 11/00 | (2006.01) |
| C11D 11/00 | (2006.01) |

(52) U.S. Cl.
CPC .............. *C11D 3/222* (2013.01); *A61K 8/04* (2013.01); *A61K 8/73* (2013.01); *A61Q 5/02* (2013.01); *A61Q 11/00* (2013.01); *A61Q 19/10* (2013.01); *C08B 37/0009* (2013.01); *C11D 3/0021* (2013.01); *C11D 3/0036* (2013.01); *C11D 3/3715* (2013.01); *C11D 11/0017* (2013.01); *C11D 11/0023* (2013.01); *C11D 17/003* (2013.01); *C11D 17/0013* (2013.01); *C11D 17/0026* (2013.01); *A61K 2800/10* (2013.01); *A61K 2800/594* (2013.01); *A61K 2800/596* (2013.01)

(58) Field of Classification Search
CPC .. C11D 1/00; C11D 3/22; C11D 3/386; C11D 3/37; B08B 3/04; A61K 8/04; A61K 8/73
See application file for complete search history.

(56) References Cited

U.S. PATENT DOCUMENTS

| | | |
|---|---|---|
| 2,817,592 A | 12/1957 | Novak et al. |
| 2,988,782 A | 6/1961 | Esperanza et al. |
| 2,999,788 A | 9/1961 | Winthrop |
| 3,068,527 A | 12/1962 | Winthrop |
| 3,114,747 A | 12/1963 | Esperanza |
| 3,897,574 A | 7/1975 | Pass |
| 4,234,627 A | 11/1980 | Schilling |
| 4,306,059 A | 12/1981 | Yokobayashi et al. |
| 4,501,886 A | 2/1985 | O'Brien |
| 4,514,461 A | 4/1985 | Woo |
| RE32,713 E | 7/1988 | Woo |
| 4,882,220 A | 11/1989 | Ono et al. |
| 4,917,920 A | 4/1990 | Ono et al. |
| 4,946,700 A | 8/1990 | Taguchi et al. |
| 4,963,298 A | 10/1990 | Allen et al. |
| 5,097,017 A | 3/1992 | Konwinski |

(Continued)

FOREIGN PATENT DOCUMENTS

| | | |
|---|---|---|
| CN | 102176896 A | 9/2011 |
| CN | 102959068 A | 3/2013 |

(Continued)

OTHER PUBLICATIONS

Applied Fibre Science, F. Happey, Ed., Chapter 8, E. Atkins, Academic Press, New York, 1979 (Book not included).
Bao et al., "Chemical Modifications of the (1->3)-@a-d-glucan from Spores of Ganoderma Lucidum and Investigation of Their Physicochemical Properties and Immunological Activity", Carbohydrate Rese, Nov. 8, 2001, vol. 336, No. 2, pp. 127-140.
Becker, W., "Solvent Extraction of Soybeans", JAOCS, 55 (1978) p. 754-761.
Cumpstey, "Chemical Modification of Polysaccharides", Organic Chemistry, Jan. 1, 2013, vol. 2013, pp. 1-27.
International Preliminary Report on Patentability, PCT/US2016/033245, Agnes Wittmann-Regis, Authorized Officer, WIPO, 14122017.
Kiho et al, (1—>3)-alpha-D-glucan from an alkaline extract of agrocybe cylindracea and antitumor activity of its 0-(carboxymethyl)ated derivatives, Carbohydrate Research, 1989, vol. 189, pp. 273-279.

(Continued)

*Primary Examiner* — Brian P Mruk

(57) ABSTRACT

Polysaccharides can be used to provide a liquid composition with desirable rheological properties while being compatible with other ingredients, such as enzymes, that may be used in formulating the liquid composition. The polysaccharides can be i) a colloidal dispersion of poly alpha-1,3-glucan, ii) poly alpha-1,3-glucan fibrids, iii) soy polysaccharide; or iv) a combination thereof.

30 Claims, No Drawings

(56) References Cited

U.S. PATENT DOCUMENTS

| | | |
|---|---|---|
| 5,248,712 A | 9/1993 | Takeuchi et al. |
| 5,296,286 A | 3/1994 | Allen et al. |
| 5,702,942 A | 12/1997 | Leathers et al. |
| 5,712,107 A | 1/1998 | Nichols |
| 5,985,666 A | 11/1999 | Loiselle et al. |
| 6,087,559 A | 7/2000 | Nichols |
| 6,127,602 A | 10/2000 | Nichols |
| 6,127,603 A | 10/2000 | Nichols |
| 6,200,949 B1 | 3/2001 | Reijmer et al. |
| 6,284,479 B1 | 9/2001 | Nichols |
| 6,410,025 B1 | 6/2002 | Lander |
| 6,465,203 B2 | 10/2002 | Nichols |
| 6,579,839 B2 | 6/2003 | Price et al. |
| 6,645,479 B1 | 11/2003 | Shefer et al. |
| 6,967,027 B1 | 11/2005 | Heux et al. |
| 7,000,000 B1 | 2/2006 | O'Brien |
| 8,076,279 B2 | 12/2011 | Brand et al. |
| 8,551,378 B2 | 10/2013 | Velev et al. |
| 8,642,757 B2 | 2/2014 | O'Brien et al. |
| 8,828,689 B2 | 9/2014 | Caimi et al. |
| 8,835,374 B2 | 9/2014 | Guida et al. |
| 8,871,474 B2 | 10/2014 | Payne et al. |
| 8,962,282 B2 | 2/2015 | Caimi et al. |
| 9,034,092 B2 | 5/2015 | O'Brien |
| 9,080,195 B2 | 7/2015 | O'Brien et al. |
| 9,096,956 B2 | 8/2015 | Shiflett et al. |
| 9,139,718 B2 | 9/2015 | Paullin et al. |
| 9,175,423 B2 | 11/2015 | O'Brien et al. |
| 9,212,301 B2 | 12/2015 | O'Brien et al. |
| 9,278,988 B2 | 3/2016 | Kasat et al. |
| 9,334,584 B2 | 5/2016 | O'Brien et al. |
| 9,365,955 B2 | 6/2016 | Opper |
| 9,403,917 B2 | 8/2016 | Kasat et al. |
| 9,540,747 B2 | 1/2017 | O'Brien |
| 9,562,112 B2 | 2/2017 | Landschutze et al. |
| 9,644,322 B2 | 5/2017 | Massouda |
| 9,670,290 B2 | 6/2017 | Landschutze et al. |
| 9,695,253 B2 | 7/2017 | Nambiar et al. |
| 9,701,800 B2 | 7/2017 | Dumberger et al. |
| 9,708,417 B2 | 7/2017 | Cormier et al. |
| 9,714,403 B2 | 7/2017 | Nagy et al. |
| 9,719,121 B2 | 8/2017 | Fake et al. |
| 9,771,548 B2 | 9/2017 | Nagy et al. |
| 9,957,334 B2 | 5/2018 | Dennes et al. |
| 9,982,284 B2 | 5/2018 | Nagy et al. |
| 10,005,850 B2 | 6/2018 | Kasat et al. |
| 10,030,323 B2 | 7/2018 | Durnberger et al. |
| 10,059,779 B2 | 8/2018 | Nambiar et al. |
| 10,072,100 B2 | 9/2018 | Nambiar et al. |
| 10,087,479 B2 | 10/2018 | Fake et al. |
| 10,117,937 B2 | 11/2018 | Yao et al. |
| 10,428,362 B2 | 10/2019 | Nagy et al. |
| 2003/0158344 A1 | 8/2003 | Rodriques et al. |
| 2003/0165692 A1 | 9/2003 | Koch et al. |
| 2003/0195133 A1 | 10/2003 | Shefer et al. |
| 2003/0203829 A1 | 10/2003 | Shefer et al. |
| 2003/0215417 A1 | 11/2003 | Uchiyama et al. |
| 2003/0216488 A1 | 11/2003 | Uchiyama et al. |
| 2004/0071742 A1 | 4/2004 | Popplewell et al. |
| 2004/0071746 A1 | 4/2004 | Popplewell et al. |
| 2004/0072720 A1 | 4/2004 | Brain et al. |
| 2004/0087477 A1 | 5/2004 | Ness |
| 2004/0091581 A1 | 5/2004 | Joly et al. |
| 2004/0106536 A1 | 6/2004 | Mane et al. |
| 2006/0127328 A1 | 6/2006 | Monsan et al. |
| 2008/0095731 A1 | 4/2008 | Mitra |
| 2010/0093584 A1* | 4/2010 | Brand .............. A61K 8/732 510/123 |
| 2011/0014345 A1 | 1/2011 | Pilling |
| 2011/0189346 A1 | 8/2011 | Pilling et al. |
| 2011/0319310 A1 | 12/2011 | Labeque |
| 2013/0087938 A1 | 4/2013 | O'Brien et al. |
| 2013/0157316 A1 | 6/2013 | Caimi et al. |
| 2013/0161562 A1 | 6/2013 | O'Brien et al. |
| 2013/0161861 A1 | 6/2013 | O'Brien et al. |
| 2013/0168895 A1 | 7/2013 | Opper |
| 2013/0196384 A1 | 8/2013 | Caimi et al. |
| 2013/0214443 A1 | 8/2013 | Shiflett et al. |
| 2013/0244287 A1 | 9/2013 | O'Brien et al. |
| 2013/0244288 A1 | 9/2013 | O'Brien et al. |
| 2013/0313737 A1 | 11/2013 | O'Brien |
| 2014/0087431 A1 | 3/2014 | Payne et al. |
| 2014/0113821 A1 | 4/2014 | Gu et al. |
| 2014/0179913 A1 | 6/2014 | Paullin et al. |
| 2014/0187766 A1 | 7/2014 | Kasat et al. |
| 2014/0187767 A1 | 7/2014 | Kasat et al. |
| 2014/0323715 A1 | 10/2014 | Kasat et al. |
| 2015/0126730 A1 | 5/2015 | O'Brien |
| 2015/0191550 A1 | 7/2015 | Mishra et al. |
| 2015/0225877 A1 | 8/2015 | O'Brien |
| 2015/0232785 A1* | 8/2015 | Paullin .............. C09D 105/00 510/299 |
| 2015/0240278 A1 | 8/2015 | Nagy et al. |
| 2015/0259439 A1 | 9/2015 | Nambiar et al. |
| 2015/0299339 A1 | 10/2015 | Shibakami et al. |
| 2015/0353649 A1 | 12/2015 | Paullin et al. |
| 2015/0368594 A1 | 12/2015 | Nagy et al. |
| 2016/0053061 A1 | 2/2016 | Durnberger et al. |
| 2016/0053406 A1 | 2/2016 | Durnberger et al. |
| 2016/0060792 A1 | 3/2016 | Durnberger et al. |
| 2016/0122445 A1 | 5/2016 | Nambiar et al. |
| 2016/0138195 A1 | 5/2016 | Kraft et al. |
| 2016/0138196 A1 | 5/2016 | Roder et al. |
| 2016/0144065 A1 | 5/2016 | Roder et al. |
| 2016/0175811 A1 | 6/2016 | Behabtu et al. |
| 2016/0177471 A1 | 6/2016 | Kraft et al. |
| 2016/0230348 A1 | 8/2016 | Massouda |
| 2016/0251453 A1 | 9/2016 | Kasat et al. |
| 2016/0304629 A1 | 10/2016 | Kasat et al. |
| 2016/0311935 A1 | 10/2016 | Dennes et al. |
| 2016/0326268 A1 | 11/2016 | Cormier et al. |
| 2016/0326269 A1 | 11/2016 | Dennes et al. |
| 2016/0333117 A1 | 11/2016 | Massouda et al. |
| 2016/0333157 A1 | 11/2016 | Massouda et al. |
| 2017/0167063 A1 | 6/2017 | Behabtu |
| 2017/0196231 A1 | 7/2017 | Massouda et al. |
| 2017/0198108 A1 | 7/2017 | Mishra et al. |
| 2017/0198109 A1 | 7/2017 | Mishra et al. |
| 2017/0198322 A1 | 7/2017 | Cheng et al. |
| 2017/0198323 A1 | 7/2017 | Cheng et al. |
| 2017/0198324 A1 | 7/2017 | Cheng et al. |
| 2017/0204203 A1 | 7/2017 | Massouda et al. |
| 2017/0204232 A1 | 7/2017 | Mishra |
| 2017/0204442 A1 | 7/2017 | Dicosimo et al. |
| 2017/0208823 A1 | 7/2017 | Massouda et al. |
| 2017/0218093 A1 | 8/2017 | Cheng et al. |
| 2017/0267787 A1 | 9/2017 | Nambiar et al. |
| 2017/0298303 A1 | 10/2017 | Nagy et al. |
| 2017/0362345 A1 | 12/2017 | Behabtu et al. |
| 2018/0021238 A1 | 1/2018 | Huh et al. |
| 2018/0049457 A1 | 2/2018 | Cheng et al. |
| 2018/0066214 A1 | 3/2018 | Nagy et al. |
| 2018/0119357 A1 | 5/2018 | Behabtu et al. |
| 2018/0223002 A1 | 8/2018 | Dennes et al. |
| 2018/0230241 A1 | 8/2018 | Johnson et al. |
| 2018/0273731 A1 | 9/2018 | Opietnik et al. |
| 2019/0186049 A1 | 6/2019 | Durnberger et al. |
| 2019/0218373 A1 | 7/2019 | Opietnik et al. |

FOREIGN PATENT DOCUMENTS

| | | |
|---|---|---|
| EP | 1393706 A1 | 3/2004 |
| EP | 1328616 B1 | 7/2008 |
| WO | 89/09259 A1 | 10/1989 |
| WO | 2005/053765 A1 | 6/2005 |
| WO | 2006/036092 A1 | 4/2006 |
| WO | 2013/036918 A2 | 3/2013 |
| WO | 2013/036968 A1 | 3/2013 |
| WO | 2013/052730 A1 | 4/2013 |
| WO | 2013/096502 A1 | 6/2013 |
| WO | 2013/096511 A1 | 6/2013 |
| WO | 2013/101854 A1 | 7/2013 |
| WO | 2013/177348 A1 | 11/2013 |
| WO | 2014/052386 A2 | 4/2014 |

(56) References Cited

FOREIGN PATENT DOCUMENTS

| | | |
|---|---|---|
| WO | 2014/077340 A1 | 5/2014 |
| WO | 2014/099724 A1 | 6/2014 |
| WO | 2014/105696 A1 | 7/2014 |
| WO | 2014/105698 A1 | 7/2014 |
| WO | 2014/161018 A1 | 10/2014 |
| WO | 2014/161019 A1 | 10/2014 |
| WO | 2014/165881 A1 | 10/2014 |
| WO | 2014/201479 A1 | 12/2014 |
| WO | 2014/201480 A1 | 12/2014 |
| WO | 2014/201481 A1 | 12/2014 |
| WO | 2014/201482 A1 | 12/2014 |
| WO | 2014/201483 A1 | 12/2014 |
| WO | 2014/201484 A1 | 12/2014 |
| WO | 2015/069828 A1 | 5/2015 |
| WO | 2015/094402 A1 | 6/2015 |
| WO | 2015/095046 A1 | 6/2015 |
| WO | 2015/095358 A2 | 6/2015 |
| WO | 2015/103531 A1 | 7/2015 |
| WO | 2015/109064 A1 | 7/2015 |
| WO | 2015/109066 A1 | 7/2015 |
| WO | 2015/109164 A1 | 7/2015 |
| WO | 2015/123323 A1 | 8/2015 |
| WO | 2015/123327 A1 | 8/2015 |
| WO | 2015/130881 A1 | 9/2015 |
| WO | 2015/130883 A1 | 9/2015 |
| WO | 2015/138283 A1 | 9/2015 |
| WO | 2015/183714 A1 | 12/2015 |
| WO | 2015/183721 A1 | 12/2015 |
| WO | 2015/183722 A1 | 12/2015 |
| WO | 2015/183724 A1 | 12/2015 |
| WO | 2015/183726 A1 | 12/2015 |
| WO | 2015/183729 A1 | 12/2015 |
| WO | 2015/195777 A1 | 12/2015 |
| WO | 2015/195960 A1 | 12/2015 |
| WO | 2015/200589 A1 | 12/2015 |
| WO | 2015/200590 A1 | 12/2015 |
| WO | 2015/200593 A1 | 12/2015 |
| WO | 2015/200596 A1 | 12/2015 |
| WO | 2015/200605 A1 | 12/2015 |
| WO | 2015/200612 A1 | 12/2015 |
| WO | 2016/073732 A1 | 5/2016 |
| WO | 2016/105971 A1 | 6/2016 |
| WO | 2016/106011 A1 | 6/2016 |
| WO | 2016/106068 A1 | 6/2016 |
| WO | 2016/126685 A1 | 8/2016 |
| WO | 2016/133734 A1 | 8/2016 |
| WO | 2016/160737 A1 | 10/2016 |
| WO | 2016/160738 A2 | 10/2016 |
| WO | 2016/160740 A1 | 10/2016 |

OTHER PUBLICATIONS

Kralj et al. "Glucan Synthesis in the Genus Lactobacillus: isolation and characterization of glucansucrase genes, enzymes and glucan products from six differenct strains", Microbiology, vol. 150, pp. 3681-3690 (2004).
Ogawa et al., 'Conformation of (1-3)-to-glucan tribenzoate,' Biosci Biotech Biochem, 1993, vol. 57 (10), pp. 1663-1665.
Ogawa et al., 'Crystal structure of (1->3)-alpha-d-glucan,' Water-soluble polymers: synthesis, solution properties and applications, American Chemical Society, Jan 1, 1980, vol. 141, pp. 353-362.
Ogawa et al., 'Molecular and crystal structure of the regenerated form of (I>3)-alpha-d-glucan; International Journal of Biological Macromolecules,' Feb. 1, 1981, vol. 3, No. 1, pp. 31-36.
Ogawa et al., 'X-ray diffraction data for (1>3)-alpha-d-glucan triacetate,' Carbohydrate Polymers, Jan. 1, 1983, vol. 3, No. 4, pp. 287-297.
Ogawa et al., 'X-ray diffraction data for (I>3)-alpha-d-glucan,' Carbohydrate Research, Oct. 1, 1979, vol. 75, pp. C13-C16.
PCT International Search Report and Written Opinion issued for PCT/US2013/076905, dated Mar. 4, 2014.
PCT International Search Report and Written Opinion issued for PCT/US2013/076919, dated Mar. 3, 2014.
PCT International Search Report and Written Opinion issued for PCT/US2014/044281, dated Sep. 11, 2014.
PCT International Search Report and Written Opinion issued for PCT/US2015/010139, dated Apr. 29, 2015.
PCT International Search Report and Written Opinion issued for PCT/US2015/011546, dated May 28, 2015.
PCT International Search Report and Written Opinion issued for PCT/US2015/011551, dated Jul. 9, 2015.
PCT International Search Report and Written Opinion issued for PCT/US2015/011724, dated May 15, 2015.
PCT International Search Report and Written Opinion issued for PCT/US2015/037622, dated Sep. 22, 2015.
PCT International Search Report and Written Opinion issued for PCT/US2015/037624, dated Oct. 12, 2015.
PCT International Search Report and Written Opinion issued for PCT/US2015/037628, dated Sep. 22, 2015.
PCT International Search Report and Written Opinion issued for PCT/US2015/037634, dated Sep. 22, 2015.
PCT International Search Report and Written Opinion issued for PCT/US2015/037646, dated Oct. 7, 2015.
PCT International Search Report and Written Opinion issued for PCT/US2015/037656, dated Oct. 7, 2015.
PCT International Search Report and Written Opinion issued for PCT/US2015/066317, dated Mar. 30, 2016.
PCT International Search Report and Written Opinion issued for PCT/US2016/016136, dated Apr. 4, 2016.
PCT International Search Report and Written Opinion issued for PCT/US2016/033245, dated Aug. 22, 2016.
PCT International Search Report and Written Opinion issued for PCT/US2016/033249, dated Jul. 26, 2016.
Serrato, A.G., "Extraction of Oil from Soybeans", JAOCS, 58 (1981) p. 157-159.
Shida et al., 'A (1/AR3-)-Alpha-D-Glucan isolated from the fruit bodies of lentinus edodes,' Carbohydrate Research, 1978, vol. 60, No. 1, pp. 117-127.
Shimamura et al., "Identification of Amino Acid Residues in Streptococcus mutans Glucosyltransferases Influencing the Structure of the Glucan Product", J. Bacteriology, vol. 176, No. 16, pp. 4845-4850, 1994.
Simpson et al., 'Four glucosyltransferases, GtfJ, GtfK, GtfL and GtfM from Streptococcus salivarius ATCC 25975,' Microbiology, 1995, vol. 141, pp. 1451-1460.
Striegel et al., "An SEC/MALS study of alteman degradation during size-exclusion chromatographic analysis", Anal. Bioanal. Chem. (2009), 394:1887-1893.
Synytsya et al., 'Structural analysis of glucans,' Annals of Translational Medicine, Feb. 1, 2014, vol. 2, No. 2, 14 pages.
Villares et al., 'Structural features and healthy properties of polysaccharides occurring in mushrooms,' Agriculture, Dec. 18, 2012, vol. 2, No. 4, pp. 452-471.
Zhang et al., 'Dissolution and regeneration of cellulose in NaOH/Thiourea Aqueous Solution,' J Polym Sci Part B: Polym Phys, 2002, vol. 40, pp. 1521-1529.
Zhang et al., 'Effects of urea and sodium hydroxide on the molecular weight and conformation of alpha-(1->3)-d-glucan from Lentinus edodes in aqueous solution,' Carbohydrate Research, Aug. 7, 2000, vol. 327, No. 4, pp. 431-438.

\* cited by examiner

STRUCTURED LIQUID COMPOSITIONS COMPRISING COLLOIDAL DISPERSIONS OF POLY ALPHA-1,3-GLUCAN

CROSS-REFERENCE TO RELATED APPLICATIONS

This application claims priority under 35 U.S.C. § 371 as a national phase of International Patent Application No. PCT/US2016/033245 (filed May 19, 2016; and published on Dec. 8, 2016 as Publication No. WO 2016/196021 A1), which claims priority to and the benefit of U.S. provisional patent application No. 62/169,134, filed Jun. 1, 2015; U.S. provisional patent application No. 62/169,118, filed Jun. 1, 2015; and U.S. provisional patent application No. 62/169,103, filed Jun. 1, 2015, the entirety of each of which is herein incorporated by reference.

FIELD OF THE DISCLOSURE

Polysaccharides can provide improved stability of soluble and insoluble materials in liquid compositions.

BACKGROUND

Structuring agents ("structurant") can be used as stabilizing and thickening agents for liquid compositions, e.g., liquid cleaning compositions. Structuring agents can provide a chemical network that reduces the tendency of the compositional components to coalesce and/or phase separate. Thus, structuring agents can be used to provide a liquid composition with desired viscosity and improved shelf life. However, a major challenge facing researchers is to develop a structurant that is compatible with a broad range of liquid compositions in developing a variety of potential consumer products.

Various structurants are known for providing rheological benefits to liquid compositions. Examples of desired benefits of such structurants include particle suspension, shear thinning properties, a thick appearance on the shelf, as well as stabilization of soluble and insoluble ingredients which are desired to be incorporated within the liquid composition. Known structurants include those derived from castor oil, fatty acids, esters, or fatty soap water-insoluble waxes. However, their usefulness with liquid compositions is limited due to degradation by ingredients such as enzymes, including lipase, cellulase, and the like. Polymeric structurants have also been used in such liquid compositions. However, they can result in a stringy pour profile that is undesirable to the consumer, particularly when "gel-like" viscosities are desired. Moreover, cellulose-based polymeric structurants are susceptible to various enzymes, such as cellulases.

As such, a need remains for a structurant that is compatible with a broad range of ingredients used in formulating liquid cleaning compositions such as enzymes while still achieving the desired rheological characteristics.

SUMMARY OF THE DISCLOSURE

In a first embodiment, the disclosure is directed to a liquid composition comprising: a) at least one surfactant; and b) at least one polysaccharide structurant; wherein the polysaccharide structurant is: i) a colloidal dispersion of poly alpha-1,3-glucan; ii) poly alpha-1,3-glucan fibrids; iii) soy polysaccharide; or iv) a combination thereof.

In a second embodiment, the surfactant is at least one of an anionic surfactant, a nonionic surfactant, a cationic surfactant, or a combination thereof.

In a third embodiment, the the liquid composition can comprise from 0.5 to 40 wt % of the surfactant.

In a fourth embodiment, the polysaccharide structurant can constitute between 0.1 wt % and 15 wt % of the total liquid composition.

In a fifth embodiment, the liquid composition can further comprise at least one enzyme wherein the enzyme is a cellulase, an endoglucanase with activity towards xyloglucan, or a combination thereof.

In a sixth embodiment, the liquid composition can further comprise a suspended insoluble material.

In a seventh embodiment, the liquid composition can further comprise a water-soluble polymer.

In an eight embodiment, the water-soluble polymer can be at least one of a carboxylate polymer, a polyethylene glycol polymer, a polyester soil release polymer, an amine polymer, a cellulosic polymer, a dye transfer inhibition polymer, a dye lock polymer, a hexamethylenediamine derivative polymer, or a combination thereof.

In a ninth embodiment, the liquid composition can further comprise water.

In a tenth embodiment, the disclosure relates to a process to manufacture a liquid composition comprising at least one surfactant and at least one polysaccharide structurant, the process comprising the steps of: (a) providing a liquid premix comprising the surfactant; (b) providing a structuring premix comprising the polysaccharide structurant; and (c) incorporating the structuring premix into the liquid premix using high shear mixing, wherein the polysaccharide structurant is i) a colloidal dispersion of poly alpha-1,3-glucan; ii) poly alpha-1,3-glucan fibrids; iii) soy polysaccharide; or iv) a combination thereof.

In an eleventh embodiment, the structuring premix can comprise a surfactant.

In a twelfth embodiment, the disclosure relates to the use of at least one polysaccharide structurant for structuring a surfactant-containing liquid composition, wherein the polysaccharide is i) a colloidal dispersion of poly alpha-1,3-glucan; ii) poly alpha-1,3-glucan fibrids; iii) soy polysaccharide; or iv) a combination thereof.

In a thirteenth embodiment, the disclosure relates to a method for treating a substrate by contacting the substrate with a liquid composition comprising: a) at least one surfactant; and b) at least one polysaccharide structurant, wherein the polysaccharide structurant is i) a colloidal dispersion of poly alpha-1,3-glucan; ii) poly alpha-1,3-glucan fibrids; iii) soy polysaccharide; or iv) a combination thereof.

In a fourteenth embodiment, the the substrate can be a fabric, dish or hard surface.

DETAILED DESCRIPTION OF THE DISCLOSURE

The disclosures of all patent and non-patent literature cited herein are incorporated herein by reference in their entirety.

As used herein, the term "invention", "disclosure" or "disclosed invention" is not meant to be limiting, but applies generally to any of the embodiments defined in the claims or described herein. These terms are used interchangeably herein.

As used herein, the term "liquid composition" refers to any composition comprising a liquid capable of wetting and treating a substrate, such as fabric or hard surface. Liquid compositions are more readily dispersible, and can more uniformly coat the surface to be treated, without the need to first dissolve the composition, as is the case with solid compositions. Liquid compositions can flow at 25° C., and include compositions that have an almost water like viscosity, but also include "gel" compositions that flow slowly and hold their shape for several seconds or even minutes. An example of liquid composition according to the present disclosure is a liquid cleaning composition.

As used herein, the term "structuring agent" or "structurant" refers to a compound that can be used as a stabilizing and a thickening agent for liquid compositions, e.g., liquid cleaning compositions. Structuring agents can provide a chemical network that reduces the tendency of the compositional components to coalesce and/or phase separate.

As used herein, the term "surfactants" refer to compounds that lower the surface tension (or interfacial tension) between two liquids or between a liquid and a solid. Surfactants may act as detergents, wetting agents, emulsifiers, foaming agents, and dispersants.

The term "suspension" as used herein refers to a dispersion of a substance when its particles are mixed with but undissolved in a fluid or solid.

As used herein, the term "colloidal dispersion" refers to a heterogeneous system having a dispersed phase and a dispersion medium, i.e., microscopically dispersed insoluble particles are suspended throughout another substance. An example of a colloidal dispersion in water is a hydrocolloid.

As used herein, the terms "poly alpha-1,3-glucan", "alpha-1,3-glucan polymer" and "glucan polymer" are used interchangeably. Poly alpha-1,3-glucan is a polymer comprising glucose monomeric units linked together by glycosidic linkages, wherein at least 50% of the glycosidic linkages are alpha-1,3-glycosidic linkages. Poly alpha-1,3-glucan is a type of polysaccharide. The structure of poly alpha-1,3-glucan can be illustrated as follows:

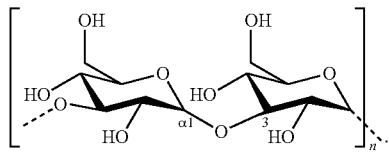

Poly alpha-1,3-glucan can be prepared using chemical methods. Alternatively, it can be prepared by extracting it from various organisms, such as fungi, that produce poly alpha-1,3-glucan. Alternatively still, poly alpha-1,3-glucan can be enzymatically produced from sucrose using one or more glucosyltransferase (gtf) enzymes (e.g., gtfJ), such as described in U.S. Pat. No. 7,000,000, and U.S. Patent Appl. Publ. Nos. 2013/0244288 and 2013/0244287 (all of which are incorporated herein by reference), for example.

The percentage of glycosidic linkages between the glucose monomer units of poly alpha-1,3-glucan used to prepare poly alpha-1,3-glucan compounds herein that are alpha-1,3 is at least 50%, 60%, 70%, 80%, 90%, 95%, 96%, 97%, 98%, 99%, or 100% (or any integer value between 50% and 100%). In such embodiments, accordingly, poly alpha-1,3-glucan has less than 50%, 40%, 30%, 20%, 10%, 5%, 4%, 3%, 2%, 1% or 0% (or any integer value between 0% and 50%) of glycosidic linkages that are not alpha-1,3.

As used herein, the term "poly alpha-1,3-glucan slurry" refers to an aqueous mixture comprising the components of a glucosyltransferase enzymatic reaction such as poly alpha-1,3-glucan, sucrose, one or more glucosyltransferase enzymes, glucose and fructose.

As used herein, the term "poly alpha-1,3-glucan wet cake" refers to poly alpha-1,3-glucan that has been separated from a slurry and washed with water or an aqueous solution. Poly alpha-1,3-glucan is not dried when preparing a wet cake. Water remains on the surface of glucan solid particles and trapped between particles. Whereas the glucan colloidal dispersion is a pourable liquid, the wet cake has a soft solid-like consistency.

As used herein, the term "colloidal dispersion" refers to a heterogeneous system having a dispersed phase and a dispersion medium, i.e., microscopically dispersed insoluble particles are suspended throughout another substance. An example of a colloidal dispersion in water is a hydrocolloid. The colloidal dispersion may be a stable colloidal dispersion or an unstable colloidal dispersion. The stable colloidal dispersion is stable at room temperature and/or at elevated temperature, for example, between 40 and 50° C. for a period of at least one month with no visible settling. The unstable dispersion, under the same conditions, may see at least a portion of the poly alpha-1,3-glucan settle out of the dispersion. Agitation of the settled material will generally re-form the colloidal dispersion. In some embodiments, the colloidal dispersion is a stable dispersion. In other embodiments, the colloidal dispersion is an unstable dispersion.

The colloidal dispersion of alpha-1,3-glucan comprises poly alpha-1,3-glucan and a solvent. In some embodiments, the colloidal dispersion consists essentially of poly alpha-1,3-glucan and a solvent. In other embodiments, the colloidal dispersion comprises less than 1% by weight of sucrose and/or fructose, wherein the percentage by weight is based on the total amount of the colloidal dispersion.

The poly alpha-1,3-glucan colloidal dispersion comprises particles with an average particle diameter size of between 5 nm, 10 nm or 20 nm and 100 nm, 150 nm or 200 nm. Preferably the particles have an average particle diameter size of between 5 nm and 200 nm and more preferably between 10 nm and 100 nm. The particles can have a spherical or cylindrical shape. Typically, the particles are substantially spherical in shape. By substantially is meant that greater than 50% of the particles are spherical in shape. The particles can form aggregates with an average aggregate diameter size of between 10 nm, 100 nm, 1 μm or 10 μm and 100 μm, 150 μm or 300 μm. Preferably the aggregates have an average aggregate diameter size of between 10 nm and 250 μm and more preferably between 10 μm and 225 μm. In all cases, the average size refers to the D50 particle size, or the particle size in which 50% of the particles are larger and 50% of the particles are smaller than the D50 value.

The solvent for the colloidal dispersion can be water. In other embodiments, the solvent can be a combination of water and less than 50% by weight of one or more water-miscible organic solvents, for example, methanol, ethanol, isopropanol, propanol, acetone, ethylene glycol, acetic acid, tetrahydrofuran, dimethyl sulfoxide, dimethyl formamide or a combination thereof, wherein the percentage by weight is based on the total amount of the solvent.

The term "fibrids", as used herein, means nongranular, fibrous or film-like particles with at least one of their three dimensions being of minor magnitude relative to the largest dimension. The terms "fibrids", "poly alpha-1,3-glucan fibrids" and "fribillated glucan" are used interchangeably herein.

These fibrids can be prepared by precipitation of a solution of poly alpha-1,3-glucan by adding the solution to a non-solvent under shear, preferably, high shear. The term "non-solvent" as used herein means a solvent that the poly alpha-1,3-glucan is relatively insoluble, for example has a solubility of less than or equal to 0.5 or 0.4 or 0.3 or 0.2 or 0.1 grams/liter. Examples of suitable non-solvents include methanol, ethanol, isopropanol, acetone, aqueous acidic solution, water, etc.

Fibrids of the disclosure can be made by the addition of a glucan-containing solution into a precipitating bath of liquid that is immiscible with poly alpha-1,3-glucan. In some embodiments, the precipitating bath can comprise acid or alkali aqueous solution or alcohol.

The addition of the glucan containing solution to the precipitating bath can be accomplished using any standards methods known to those skilled in the art. For example, direct injection can be used.

The stream of polymer solution is subjected to shearing forces and turbulence as the fibrids precipitated in the form of a suspension by using a non-solvent (i.e., a liquid that is not a good solvent). In some embodiments, the precipitating bath can comprise acid or alkali aqueous solution or alcohol.

It should be noted that the fibrids can be isolated by filtering the suspension. Optionally, the isolated fibrids can be dried. It is believed that it is possible to resuspend the dried fibrids either by adding a component such as carboxymethyl cellulose and the like or by functionalizing the fibrids by adding certain groups that would facilitate resuspension in a liquid.

It is possible to control viscosity of the suspension containing fibrids as well as the size and/or shape of the fibrids by controlling one or more process parameters such as dope concentration, type of solvent, type of mixer, mixing speed, pH of precipitation bath, rate of addition of solution containing polymer, amount of non-solvent used, duration of mixing, neutralization rate and concentration of neutralizer.

The term "dope" as used herein refers to the solution containing alpha-1,3-glucan polymer. A dope can be prepared by mixing polymer into a solvent. Thus, as well known to those skilled in the art, dope concentration refers to varying the amount of polymer mixed into the solvent.

The types of solvent that can be used to produce the solution of alpha-1,3-glucan polymer can include, but are not limited to, an aqueous basic solution containing components such as sodium hydroxide, potassium hydroxide, lithium hydroxide, etc.

Any type of mixer can be used to produce the fibrids. For example, a Waring blender can be used. The speed and duration of the mixing can be adjusted in order to control the viscosity of the suspension containing the fibrids.

The pH of the precipitation bath can be adjusted from very acidic to neutral to basic depending upon the solvent chosen in which to mix the poly alpha-1,3-glucan.

Amount of non-solvent as well as the rate at which it is added can also be varied.

Furthermore, the rate of neutralization and amount of neutralizer used can also be adjusted. The term "neutralization" means the process of making a solution neutral by adding a base to an acidic solution or adding acid to a basic solution. The term "neutralizer" means any agent that decreases the pH of a basic mixture or increases the pH of an acidic mixture.

As used herein, the term "soy polysaccharide" and "soy fiber" are used interchangeably, and refer to the high molecular weight, water-insoluble polysaccharide material of soybeans. Typically, soy polysaccharide is obtained from cell wall structural components of soybeans.

For example, a soy polysaccharide production process can first comprise a step of producing white flakes from whole soybeans. Soy white flake production typically comprises: i) dehulling whole soybeans, ii) flaking the dehulled soybeans, iii) extracting soybean oil from the flaked soybeans with a solvent (e.g., organic solvent such as hexane), and 4) removing the solvent from the defatted soybeans (preferably without high heating or toasting) to produce white flakes. White flakes can also optionally be ground to soy flour, if desired, prior to the next step (protein extraction). Various procedures useful herein for producing soy white flakes are disclosed in, for example, U.S. Pat. Nos. 5,097,017 and 3,897,574, as well as in Serrato (J. Am. Oil Chem. Soc. 58:157-159) and Becker (J. Am. Oil Chem. Soc. 55:754-761), all of which are incorporated herein by reference.

Protein extraction can follow production of white flakes. The first step of protein extraction, which typically produces soy polysaccharide, comprises mixing white flakes with water and a base (to increase pH) to form a slurry. Protein solubility is increased in the slurry due to the increased pH. The slurry is then subjected to a process for separating the liquid (comprising protein and soluble sugar fractions) from the solids (comprising insoluble polysaccharide fraction), such as by decanting, centrifugation, and/or filtration. Solid material ("spent flake") obtained by this process can optionally be subjected to another round of alkaline slurry formation followed by liquid removal to further remove protein and other soluble components. Solid material resulting from one or more of the foregoing protein extractions comprises soy polysaccharide, and is suitable for processes disclosed herein involving soy polysaccharide. A soy polysaccharide preparation can optionally be washed (once or multiple times), dried, and/or powderized prior to its use for producing oxidized soy polysaccharide compounds. Dry soy polysaccharide can range from off-white (e.g., light brown, tan) to brown in color.

While most material in a dry soy polysaccharide preparation is polysaccharide material, other components can optionally be present, such as protein, lipid, and ash. It is believed that this residual soy material, which in some circumstances is not completely removed during soy protein/oil acquisition processing, does not greatly inhibit processes disclosed herein employing soy polysaccharide material. Thus, a soy polysaccharide preparation herein can comprise at least about 50, 55, 60, 65, 70, 75, 76, 77, 78, 79, 80, 81, 82, 83, 84, 85, 86, 87, 88, 89, 90, 91, 92, 93, 94, 95, 96, 97, 98, or 99 wt % insoluble polysaccharide, for example, as measured on a dry basis (e.g., less than 1 or 0.5 wt % water). With respect to the presence of residual soy components, a soy polysaccharide preparation in some embodiments can comprise (i) less than about 25, 20, 15, 14, 13, 12, 11, 10, 9, 8, 7, 6, 5, 4, 3, 2, or 1 wt % protein; (ii) less than about 5, 4, 3, 2, or 1 wt % ash; (iii) less than about 10, 9, 8, 7, 6, 5, 4, 3, 2, or 1 wt % lipid; and/or (iv) less than about 5, 4, 3, 2, 1, or 0.5 wt % low molecular weight, water-soluble sugars, as measured on a dry basis (e.g., less than 1 or 0.5 wt % water). Other residual soy components that can be present within a soy polysaccharide preparation herein include isoflavones, lignans, phytosterols, coumestans, saponins and/or phytates, for example. In some embodiments, a soy polysaccharide preparation comprises about 78-82 wt % insoluble polysaccharide, 10-14 wt % protein, 4-6 wt % ash, and 1-2 wt % lipid.

Polysaccharide component(s) of a soy polysaccharide preparation useful herein can comprise regions of one or more different types of polysaccharide chains, such as galacturonan, rhamnogalacturonan, arabinogalactan and/or arabinan. Other polysaccharide sub-regions of soy polysaccharide may comprise galactan, xylogalacturonan, xylan, xyloglucan and/or cellulose, for example. Soy polysaccharide herein can comprise arabinose (Ara), galactose (Gal), xylose (Xyl), and galacturonic acid (GalA) as a majority of constituent monosaccharide monomeric units, as well as smaller amounts of rhamnose (Rha), glucose (Glc), fucose (Fuc) and mannose (Man). In certain embodiments, soy polysaccharide can comprise by weight ~21-28% Ara, ~14-42% Gal, ~10-35% GalA, ~5-17% Xyl, ~2-6% Rha, ~1-4% Fuc, ~1-4% Man, and/or ~1-6% Glc. Soy polysaccharide in certain other embodiments can comprise by weight ~11-13% Ara, ~40-42% Gal, ~30-32% Glc and Man, and ~2.5-3.5% Xyl. Soy polysaccharide can comprise polysaccharide sub-regions, monosaccharide monomers, and glycosidic linkage profiles as disclosed in Li et al. (*Molecules* 17:753-761), for example, which is incorporated herein by reference.

As used herein, the term "viscosity" refers to the measure of the extent to which a fluid or an aqueous composition resists a force tending to cause it to flow. Various units of viscosity that can be used herein include centipoise (cPs) and Pascal-second (Pa·s). A centipoise is one one-hundredth of a poise; one poise is equal to 0.100 $kg·m^{-1}·s^{-1}$. Thus, the terms "viscosity modifier" and "viscosity-modifying agent" as used herein refer to anything that can alter/modify the viscosity of a fluid or aqueous composition.

Viscosity can be measured at any temperature between 3° C. to 110° C. (or any integer between 3 and 110° C.). Alternatively, viscosity can be measured at a temperature between 4° C. to 30° C., or 20° C. to 25° C. Viscosity can be measured at atmospheric pressure (about 760 torr) or any other higher or lower pressure.

The viscosity can be measured using a viscometer or rheometer, or using any other means known in the art. It would be understood by those skilled in the art that a rheometer can be used to measure the viscosity of those hydrocolloids and aqueous solutions of the disclosure that exhibit shear thinning behavior or shear thickening behavior (i.e., liquids with viscosities that vary with flow conditions). The viscosity of such embodiments can be measured at a rotational shear rate of 10 to 1000 rpm (revolutions per minute) (or any integer between 10 and 1000 rpm), for example. Alternatively, viscosity can be measured at a rotational shear rate of 10, 60, 150, 250, or 600 rpm.

As used herein, the term "shear thinning behavior" refers to a decrease in the viscosity as shear rate increases. The term "shear thickening behavior" as used herein refers to an increase in the viscosity as shear rate increases. "Shear rate" herein refers to the rate at which a progressive shearing deformation is applied to the liquid composition. A shearing deformation can be applied rotationally.

As used herein, the terms "percent by weight (% by wt.)", "weight percentage (wt %)" and "weight-weight percentage (% w/w)" are used interchangeably. Percent by weight refers to the percentage of a material on a mass basis as it is comprised in a composition, mixture or solution.

Unless otherwise noted, all component, premix, or composition levels are in reference to the active portion of that component, premix, or composition, and are exclusive of impurities, for example, residual solvents or by-products, which may be present in commercially available sources of such components or compositions.

Polysaccharide structurants have been found to be useful in achieving the desired rheological properties in liquid compositions, especially, surfactant-containing liquid cleaning compositions. The polysaccharide structurants i) colloidal dispersions of poly alpha-1,3-glucan, ii) poly alpha-1,3-glucan fibrids, and iii) soy polysaccharides are compatible with a broad range of typical consumer product ingredients, including detersive enzymes, while still providing such desirable rheological properties such as good structuring and pourability. Furthermore, the polysaccharide structurants are not degraded by detersive enzymes and its structuring capability is resilient to the addition of typical adjunct ingredients typically used for consumer product applications.

In some embodiments, the disclosure relates to a liquid composition comprising:
a) at least one surfactant; and
b) at least one polysaccharide structurant;
wherein the polysaccharide structurant is:
i) a colloidal dispersion of poly alpha-1,3-glucan;
ii) poly alpha-1,3-glucan fibrids;
iii) soy polysaccharide; or
iv) a combination thereof.

The liquid compositions, which can be structured using the polysaccharide structurants, have a high low-shear viscosity. Thus, the polysaccharide structurants are also effective at suspending particulates or droplets in liquid compositions, including solid particulates such as perfume microcapsules, and the like, and liquid droplets such as perfume droplets, other oils, and the like.

The polysaccharide structurants i), ii) and/or iii) disclosed herein can be present in the liquid composition at a weight percentage (wt %) of at least 0.01%, 0.05%, 0.1%, 0.2%, 0.3%, 0.4%, 0.5%, 0.6%, 0.7%, 0.8%, 0.9%, 1.0%, 1.2%, 1.4%, 1.6%, 1.8%, 2.0%, 2.5%, 3.0%, 3.5%, 4.0%, 4.5%, 5%, 6%, 7%, 8%, 9%, 10%, 11%, 12%, 13%, 14% or 15%.

A non-limiting example of a household product or industrial product is a liquid detergent. The polysaccharide structurants i), ii) and/or iii) can be used as a structuring agent or thickener to stabilize the components in liquid detergent formulation.

Liquid compositions, comprising the polysaccharide structurants i), ii) and/or iii) are typically thixotropic, providing good suspension of particles and droplets, while easily flowing under shear. As a result, the polysaccharide structurants i), ii) and/or iii) are particularly suitable for surfactant-containing liquid compositions, since it stabilizes suspended insoluble material in the liquid composition, while reducing phase separation, and being compatible with a wide variety of adjuncts, including enzymes. Moreover, the polysaccharide structurants i), ii) and/or iii) are believed to also improve deposition of actives, including perfumes, perfume microcapsules, and the like.

The liquid compositions typically comprise from 0.05 to 10 wt %, preferably from 0.1 to 5 wt %, more preferably from 0.15 to 2 wt % of the polysaccharide structurants i), ii) and/or iii).

Suitable liquid compositions include consumer products such as, for example, products for treating fabrics, including laundry detergent compositions, and rinse additives such as fabric softeners; hard surface cleaners including dishwashing compositions, floor cleaners, and toilet bowl cleaners. Such liquid compositions may provide a cleaning benefit, and hence can comprise detersive surfactant, so as to provide a noticeable cleaning benefit. Most preferred are liquid laundry detergent compositions, which are capable of cleaning a fabric, such as in a domestic washing machine.

A suitable liquid composition can include solids or gases in suitably subdivided form, but the overall liquid composition excludes product forms which are non-liquid overall, such as tablets or granules. The liquid compositions preferably have densities in the range from of 0.9 to 1.3 $g/cm^3$, more preferably from 1.00 to 1.10 g/cm$^3$, excluding any solid additives but including any bubbles, if present.

Preferably, the liquid composition comprises from 1% to 95% by weight of water, non-aminofunctional organic solvent, or a combination thereof. For concentrated liquid compositions, the composition preferably comprises from 15% to 70%, more preferably from 20% to 50%, most preferably from 25% to 45% by weight of water, non-aminofunctional organic solvent, or a combination thereof. Alternatively, the liquid composition may be a low water liquid composition. Such low water liquid compositions can comprise less than 20%, preferably less than 15%, more preferably less than 10% by weight of water.

A liquid composition of the present invention may comprise from 2% to 40%, more preferably from 5% to 25% by weight of a non-aminofunctional organic solvent.

In some embodiments, the liquid composition can be encapsulated in a water soluble film, to form a unit dose article. Such unit dose articles comprise a liquid composition of the present invention, wherein the liquid composition is a low water liquid composition, and the liquid composition is enclosed in a water-soluble or dispersible film.

The unit dose article may comprise one compartment, formed by the water-soluble film which fully encloses at least one inner volume, the inner volume comprising the low water liquid composition. The unit dose article may optionally comprise additional compartments comprising further low water liquid compositions, or solid compositions. A multi-compartment unit form may be desirable for such reasons as separating chemically incompatible ingredients or where it is desirable for a portion of the ingredients to be released earlier or later. The unit-dose articles can be formed using any means known in the art.

Unit dose articles, wherein the low water liquid is a liquid laundry detergent composition are particularly preferred.

Suitable water soluble pouch materials include polymers, copolymers or derivatives thereof. The polymers, copolymers or derivatives can be at least one of, for example, polyvinyl alcohols, polyvinyl pyrrolidone, polyalkylene oxides, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatin, natural gums such as xanthum and carragum. More preferred polymers can be polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, and most preferably selected from polyvinyl alcohols, polyvinyl alcohol copolymers and hydroxypropyl methyl cellulose (HPMC), and combinations thereof.

The liquid compositions of the present invention may comprise from 0.5 to 40 wt %, preferably from 2 to 35 wt %, more preferably from 10 to 30 wt % of the surfactant.

The liquid composition comprises a surfactant wherein the surfactant is at least one of, for example, anionic surfactant, nonionic surfactant, cationic surfactant, or a combination thereof.

The liquid compositions can provide a detergency benefit. Such liquid detergent compositions typically comprise at least one surfactant wherein the surfactant is, for example, an anionic surfactant, a nonionic surfactant, or a combination thereof.

For liquid compositions which provide a detersive benefit, the preferred weight ratio of anionic to nonionic surfactant is from 100:0 (i.e. no nonionic surfactant) to 5:95, more preferably from 99:1 to 1:4, most preferably from 5:1 to 1.5:1.

The liquid detergent compositions of the present invention preferably comprise from 1 to 50%, more preferably from 5 to 40%, most preferably from 10 to 30% by weight of one or more anionic surfactants. Preferred anionic surfactant can be, for example $C_{11}$-$C_{18}$ alkyl benzene sulfonates, $C_{10}$-$C_{20}$ branched-chain and random alkyl sulphates, $C_{10}$-$C_{18}$ alkyl ethoxy sulphates, mid-chain branched alkyl sulphates, mid-chain branched alkyl alkoxy sulphates, $C_{10}$-$C_{18}$ alkyl alkoxy carboxylates comprising 1-5 ethoxy units, modified alkylbenzene sulfonate, $C_{12}$-$C_{20}$ methyl ester sulfonate, $C_{10}$-$C_{18}$ alpha-olefin sulfonate, $C_6$-$C_{20}$ sulphosuccinates, or a combination thereof. However, by nature, every anionic surfactant known in the art of detergent compositions may be used, such as those disclosed in "Surfactant Science Series", Vol. 7, edited by W. M. Linfield, Marcel Dekker. In some embodiments, the detergent compositions preferably comprise at least one sulphonic acid surfactant, such as a linear alkyl benzene sulphonic acid, or the water-soluble salt form of the acid.

The liquid compositions of the present invention preferably comprise up to 30%, more preferably from 1 to 15%, most preferably from 2 to 10% by weight of one or more nonionic surfactants. Suitable nonionic surfactants include, but are not limited to $C_{12}$-$C_{18}$ alkyl ethoxylates ("AE") including the so-called narrow peaked alkyl ethoxylates, $C_6$-$C_{12}$ alkyl phenol alkoxylates (especially ethoxylates and mixed ethoxy/propoxy), block alkylene oxide condensate of $C_6$-$C_{12}$ alkyl phenols, alkylene oxide condensates of $C_8$-$C_{22}$ alkanols and ethylene oxide/propylene oxide block polymers (PLURONIC®-BASF Corp.), as well as semi polar nonionics (e.g., amine oxides and phosphine oxides). An extensive disclosure of suitable nonionic surfactants can be found in U.S. Pat. No. 3,929,678.

The liquid composition may also include conventional detergent ingredients, for example, additional surfactants selected from amphoteric, zwitterionic, cationic surfactant, and mixtures thereof; enzymes; enzyme stabilizers; amphiphilic alkoxylated grease cleaning polymers; clay soil cleaning polymers; soil release polymers; soil suspending polymers; bleaching systems; optical brighteners; hueing dyes; particulates; perfume and other odor control agents, including perfume delivery systems; hydrotropes; foam suppressors; fabric care perfumes; pH adjusting agents; dye transfer inhibiting agents; preservatives; non-fabric substantive dyes; or a combination thereof.

The polysaccharide structurants i), ii) and/or iii) are particularly effective at stabilizing suspended insoluble material since they provide the liquid composition with a thixotropic rheology profile, and a yield stress which is sufficiently high enough to suspend such insoluble material. The liquid composition preferably comprises a sufficient amount of the polysaccharide structurants i), ii) and/or iii) to provide a yield stress of greater than 0.005 Pa, preferably from 0.01 to 1 Pa, more preferably from 0.1 to 1 Pa. As such, the aqueous structuring premixes of the present disclosure are particularly suited for stabilizing liquid compositions which further comprise suspended insoluble material. Suitable suspended insoluble material can be, for example, particulates, insoluble fluids, or a combination thereof. Suspended insoluble materials are those which have a solubility in the liquid composition of less than 1%, at a temperature of 21° C.

The particulates may be microcapsules such as perfume encapsulates, or care additives in encapsulated form. The particulates may alternatively, or additionally, take the form of insoluble ingredients such as quaternary ammonium materials, insoluble polymers, insoluble optical brighteners, enzymes, and other known benefit agents such as those found, for example, in EP1328616. The amount of particulates may be from 0.001 to up to 10 or even 20 wt %.

Microcapsules are typically added to liquid compositions in order to provide a long lasting in-use benefit to the treated substrate. Microcapsules can be added at a level of from 0.01% to 10%, more preferably from 0.1% to 2%, even more preferably from 0.15% to 0.75% of the encapsulated active, by weight of the liquid composition. In a preferred embodiment, the microcapsules are perfume microcapsules, in which the encapsulated active is a perfume. Such perfume microcapsules release the encapsulated perfume upon breakage, for instance, when the treated substrate is rubbed.

The term "microcapsule" is used herein in the broadest sense to include a core that is encapsulated by the microcapsule wall. In turn, the core comprises a benefit agent, such as a perfume. The microcapsules typically comprise a microcapsule core and a microcapsule wall that surrounds the microcapsule core. The microcapsule wall is typically formed by cross-linking formaldehyde with at least one other monomer.

The microcapsule core may optionally comprise a diluent. Diluents are material used to dilute the benefit agent that is to be encapsulated, and are hence preferably inert. That is, the diluent does not react with the benefit agent during making or use. Preferred diluents may be selected from the group consisting of: isopropylmyristate, propylene glycol, poly(ethylene glycol), or mixtures thereof.

Microcapsules, and methods of making them are disclosed in the following references: US 2003-215417 A1; US 2003-216488 A1; 2003-158344 A1; US 2003-165692 A1; US 2004-071742 A1; US 2004-071746 A1; US 2004-072719 A1; US 2004-072720 A1; EP 1393706 A1; US 2003-203829 A1; US 2003-195133 A1; US 2004-087477 A1; US 2004-0106536 A1; U.S. Pat. Nos. 6,645,479; 6,200,949; 4,882,220; 4,917,920; 4,514,461; U.S. RE 32713; U.S. Pat. No. 4,234,627.

Encapsulation techniques are disclosed in Microencapsulation: Methods and Industrial Applications, Edited by Benita and Simon (Marcel Dekker, Inc., 1996). Formaldehyde based resins such as melamine-formaldehyde or urea-formaldehyde resins are especially attractive for perfume encapsulation due to their wide availability and reasonable cost.

The microcapsules preferably have a size of from 1 micron to 75 microns, more preferably from 5 microns to 30 microns. The microcapsule walls preferably have a thickness of from 0.05 microns to 10 microns, more preferably from 0.05 microns to 1 micron. Typically, the microcapsule core comprises from 50% to 95% by weight of the benefit agent.

The liquid composition may optionally comprise a suspended insoluble fluid. Suitable insoluble fluids include silicones, perfume oils, and the like. Perfume oils provide an odour benefit to the liquid composition, or to substrates treated with the liquid composition. When added, such perfumes are added at a level of from 0.1% to 5%, more preferably from 0.3% to 3%, even more preferably from 0.6% to 2% by weight of the liquid composition. Suitable silicones include silicones which provide an anti-foam benefit, a fabric softening benefit, and combinations thereof. For improved anti-foaming or fabric softening, the silicones can be functionalized, including amino-functionalized.

The polysaccharide structurants i), ii) and/or iii) are resistant to degradation by: cellulases, endoglucanase with activity towards xyloglucan, or a combination thereof. Hence, the liquid composition can comprise at least one enzyme wherein the enzymes are cellulases, endoglucanase with activity towards xyloglucan, or a combination thereof.

Suitable cellulases include, for example, endo-beta-1,4-glucanases, cellobiohydrolases and beta-1,4-glucosidases, of bacterial or fungal origin, from any family of glycosyl hydrolase exhibiting cellulase activity. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531372, WO 96/11262, WO 96/29397, WO 98/08940. Other examples are cellulase variants such as those described in WO 94/07998, EP 0531 315, U.S. Pat. Nos. 5,457,046, 5,686,593, 5,763,254, WO 95/24471, and WO 98/12307.

Commercially available cellulases include CELLUZYME®, and CAREZYME® (Novozymes A/S), CLAZINASE®, PURADAX® EG-L and PURADAX® HA (Genencor International Inc.), and KAC®-500(B) (Kao Corporation).

In one aspect, the cellulase can include microbial-derived endoglucanases exhibiting endo-beta-1,4-glucanase activity (E.C. 3.2.1.4), including a bacterial polypeptide endogenous to a member of the genus *Bacillus* which has a sequence of at least 90%, 94%, 97% and even 99% identity to the amino acid sequence SEQ ID NO:2 in U.S. Pat. No. 7,141,403) and mixtures thereof. Suitable endoglucanases are sold under the tradenames CELLUCLEAN® and WHITEZYME® (Novozymes A/S, Bagsvaerd, Denmark). WHITEZYME® is an example of an endoglucanase exhibiting activity towards both cellulose and xyloglucan, and is a variant of a Glycosyl Hydrolase family 44 endoglucanase truncated from an assembly endogenous to *Paenibacillus polyxyma*.

Preferably, the composition comprises a cleaning cellulose belonging to Glycosyl Hydrolase family 45 having a molecular weight of from 17 kDa to 30 kDa, for example the endoglucanases sold under the tradename BIOTOUCH® NCD, DCC and DCL (AB Enzymes, Darmstadt, Germany). The cellulase may be intentionally formulated, or it may be introduced to the detergent composition as an impurity in another raw material, especially an enzyme. Commercial enzymes of many classes, for example, protease, alpha-amylase, beta-mannanase, pectate lyase and lipase, may contain additional cellulase activity as a result of the production microorganism expressing cellulase enzymes that are not fully removed during the purification steps, or through contamination from other products during the enzyme production process. The commercial protease PURAFECT® Prime (Genencor Division of Danisco) is an example of a non-cellulase enzyme which typically contains significant cellulase impurities.

Another non-intentional source of cellulase in detergent compositions is from cross-contamination in production plants, for example when changing over from a cellulase-containing formula to one with no intentionally formulated cellulase.

The liquid compositions may comprise from 0.0001% to 8% by weight of other detersive enzymes which provide improved cleaning performance and/or fabric care benefits. Such liquid compositions preferably have a pH of from 6 to 10.5. Suitable enzymes can be selected from the group consisting of: lipase, protease, amylase, mannanase, pectate lyase, xyloglucanase, and mixtures thereof, in addition to the cellulase enzyme. A preferred enzyme combination comprises a cocktail of conventional detersive enzymes such as lipase, protease, and amylase. Detersive enzymes are described in greater detail in U.S. Pat. No. 6,579,839.

The polysaccharide structurants i), ii) and/or iii) are effective at preventing the segregation of water-soluble polymers, and any resultant phase separation of the liquid composition. Hence, the liquid composition of the present invention may comprise a water-soluble polymer. Water soluble is soluble or dispersible to at least the extent of 0.01% by weight in distilled water at 25° C. The liquid composition may comprise one or more water soluble polymers.

Examples of useful polymers include, but are not limited to, carboxylate polymers, polyethylene glycol polymers, polyester soil release polymers such as terephthalate polymers, amine polymers, cellulosic polymers, dye transfer inhibition polymers, dye lock polymers such as a condensation oligomer produced by condensation of imidazole and epichlorhydrin, optionally in ratio of 1:4:1, hexamethylenediamine derivative polymers, and any combination thereof.

There can also be mentioned carboxylate polymers such as maleate/acrylate random copolymer or polyacrylate homopolymer. The carboxylate may be a polyacrylate homopolymer having a molecular weight of from 4,000 Da to 9,000 Da, or from 6,000 Da to 9,000 Da. Other suitable carboxylate polymers are co-polymers of maleic acid and acrylic acid, and may have a molecular weight in the range of from 4,000 Da to 90,000 Da.

Other carboxylate polymers that can be used are co-polymers comprising: (i) from 50 to less than 98 wt % structural units derived from one or more monomers comprising carboxyl groups; (ii) from 1 to less than 49 wt % structural units derived from one or more monomers comprising sulfonate moieties; and (iii) from 1 to 49 wt % structural units derived from one or more types of monomers selected from ether bond-containing monomers represented by formulas (I) and (II):

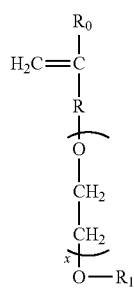

formula (I)

wherein in formula (I), $R_0$ represents a hydrogen atom or $CH_3$ group, R represents a $CH_2$, $CH_2CH_2$ group or single bond, X represents a number 0-5 provided X represents a number 1-5 when R is a single bond, and $R_1$ is a hydrogen atom or $C_1$ to $C_{20}$ organic group;

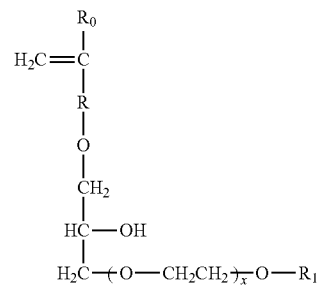

formula (II)

wherein formula (II), $R_0$ represents a hydrogen atom or $CH_3$ group, R represents a $CH_2$ group, $CH_2CH_2$ group or single bond, X represents a number 0-5, and $R_1$ is a hydrogen atom or $C_1$ to $C_{20}$ organic group.

Examples of polyethylene glycol polymers that can be used include random graft co-polymers comprising: (i) hydrophilic backbone comprising polyethylene glycol; and (ii) at least one hydrophobic side chain(s) wherein the hydrophobic side chains are, for example, $C_4$-$C_{25}$ alkyl group, polypropylene, polybutylene, vinyl ester of a saturated $C_1$-$C_6$ mono-carboxylic acid, $C_1$-$C_6$ alkyl ester of acrylic or methacrylic acid, or a combination thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is SOKALAN® HP22.

Exemplary polyester soil release polymers can have a structure comprising repeat units such as defined by one of the following structures (I), (II) or (III):

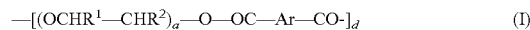

—[(OCHR$^1$—CHR$^2$)$_a$—O—OC—Ar—CO-]$_d$ (I)

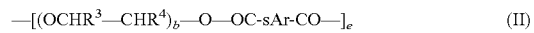

—[(OCHR$^3$—CHR$^4$)$_b$—O—OC-sAr-CO—]$_e$ (II)

—[(OCHR$^5$—CHR$^6$)$_c$—OR$^7$]$_f$ (III)

wherein:
a, b and c are from 1 to 200;
d, e and f are from 1 to 50;
Ar is a 1,4-substituted phenylene;
sAr is 1,3-substituted phenylene substituted in position 5 with $SO_3Me$;
Me is H, Na, Li, K, Mg/2, Ca/2, Al/3, ammonium, mono-, di-, tri-, tetraalkylammonium wherein the alkyl groups are $C_1$-$C_{18}$ alkyl or $C_2$-$C_{10}$ hydroxyalkyl, or any mixture thereof; and
$R^1$, $R^2$, $R^3$, $R^4$, $R^5$ and $R^6$ are independently selected from H or $C_1$-$C_{18}$ n- or iso-alkyl; and $R^7$ is a linear or branched $C_1$-$C_{18}$ alkyl, or a linear or branched $C_2$-$C_{30}$ alkenyl, or a cycloalkyl group with 5 to 9 carbon atoms, or a $C_8$-$C_{30}$ aryl group, or a $C_6$-$C_{30}$ arylalkyl group. Suitable polyester soil release polymers are terephthalate polymers having the structure of formula (I) or (II) above.

Polyester soil release polymers can include, but are not limited to, the Repel-o-tex series of polymers such as REPEL-O-TEX® SF2 (Rhodia) and/or the Texcare series of polymers such as TEXCARE® SRA300 (Clariant).

Suitable amine polymers include polyethyleneimine polymers, such as alkoxylated polyalkyleneimines, optionally comprising a polyethylene and/or polypropylene oxide block.

The water-soluble polymers can be one or more cellulosic polymers, such as polymers selected from alkyl cellulose, alkyl alkoxyalkyl cellulose, carboxyalkyl cellulose, alkyl carboxyalkyl, or a combination thereof. Suitable cellulosic polymers are selected from carboxymethyl cellulose, methyl cellulose, methyl hydroxyethyl cellulose, methyl carboxymethyl cellulose, and mixtures thereof. The carboxymethyl cellulose can have a degree of carboxymethyl substitution from 0.5 to 0.9 and a molecular weight from 100,000 Da to 300,000 Da. Another suitable cellulosic polymer is hydrophobically modified carboxymethyl cellulose, such FINNFIX® SH-1 (CP Kelco). Other suitable cellulosic polymers may have a degree of substitution (DS) of from 0.01 to 0.99 and a degree of blockiness (DB) such that either DS+DB is of at least 1.00 or $DB+2DS-DS^2$ is at least 1.20. The substituted cellulosic polymer can have a degree of substitution (DS) of at least 0.55. The substituted cellulosic polymer can have a degree of blockiness (DB) of at least 0.35. The substituted cellulosic polymer can have a DS+DB, of from 1.05 to 2.00.
Carboxymethylcellulose is an example of a substituted cellulosis polymer that can be used. Cationically modified hydroxyethyl cellulose can also be used.

The laundry detergent compositions may comprise one or more dye transfer inhibition (DTI) polymers. Suitable DTIs include polyamine N-oxide polymers, copolymers of N-vinylpyrrolidone and N-vinylimidazole, polyvinylpyrrolidone polymers, polyvinyloxazolidones and polyvinylimidazoles or mixtures thereof. The DTI polymers discussed above are well known in the art and commercially available, for example PVP-K15 and K30 (Ashland), SOKALAN® HP165, HP50, HP53, HP59, HP56K, HP56, HP66 (BASF), CHROMABOND® S-400, S403E and S-100 (Ashland), and POLYQUART® FDI (Cognis).

Suitable polymers include hexamethylenediamine derivative polymers, typically having the formula:

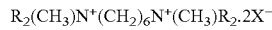

$$R_2(CH_3)N^+(CH_2)_6N^+(CH_3)R_2.2X^-$$

wherein $X^-$ is a suitable counter-ion, for example halide, chloride, bromide and R is a poly(ethylene glycol) chain having an average degree of ethoxylation of from 20 to 30. Optionally, the poly(ethylene glycol) chains may be independently capped with sulphate and/or sulfonate groups, typically with the charge being balanced by reducing the number of $X^-$ counter-ions, or (in cases where the average degree of sulphation per molecule is greater than two), introduction of $Y^+$ counter-ions, for example sodium cations.

The polysaccharide structurants i), ii) and/or iii) can be added to the liquid composition in an amount to effectively provide low-shear structuring and suspension of insoluble materials, while a polymeric structurant can be added to further increase the viscosity and to provide a shear-thinning rheology profile. The liquid composition may comprise from 0.01 to 5% by weight of such a polymeric structurant. The polymeric structurant can be naturally derived and/or synthetic. Examples of naturally derived polymeric external structurants can include, for example, hydroxyethyl cellulose, hydrophobically modified hydroxyethyl cellulose, carboxymethyl cellulose, polysaccharide derivatives and mixtures thereof. Examples of synthetic polymeric structurants can include, for example, polycarboxylates, polyacrylates, hydrophobically modified ethoxylated urethanes, hydrophobically modified non-ionic polyols and mixtures thereof. In other embodiments, the polyacrylate can be a copolymer of unsaturated mono- or dicarbonic acid and $C_1$-$C_{30}$ alkyl ester of the (meth)acrylic acid.

In other embodiments, the disclosure relates to a process to manufacture the liquid composition, wherein the process comprises the steps of: (a) providing a liquid premix comprising a surfactant; (b) providing a structuring premix comprising the polysaccharide structurants i), ii) and/or iii); and (c) incorporating the structuring premix into the liquid premix using high shear mixing. Any acceptable means of high shear mixing can be used, including the use of either continuous and non-continuous high shear mixers. High shear mixing can be provided via a dynamic mixer or static mixer.

The liquid premix comprises at least one surfactant. The liquid premix typically comprises further ingredients, typically including all the ingredients that require high shear mixing. Preferably, the structuring premix comprising at least one polysaccharide structurant i), ii), and/or iii) is the last ingredient incorporated into the liquid composition. The structuring premix is preferably incorporated into the liquid composition using high shear mixing. Preferably, the structuring premix is incorporated into the liquid composition using average shear rates of greater than $100\ s^{-1}$, preferably from $200\ s^{-1}$ to $25,000\ s^{-1}$, more preferably from $500\ s^{-1}$ to $10,000\ s^{-1}$. The residence time of mixing is preferably less than 60 s, more preferably less than 25 s, more preferably less than 5 s.

In addition to the polysaccharide structurants i), ii) and/or iii), the structuring premix may further comprise one or more surfactants. Suitable surfactants can include, for example, anionic surfactant, nonionic surfactant, cationic surfactant, or a combination thereof. In embodiments where the surfactant is present in the structuring premix, the surfactant is preferably at least one of an anionic surfactant, a nonionic surfactant, or a combination thereof. In still further embodiments, a nonionic surfactant is preferred.

For processes for manufacturing low water liquid compositions, the structuring premix may comprise non-aminofunctional solvent, such as propanediol. The addition of a non-aminofunctional solvent to the structuring premix improves the dispersion of the structuring premix into a low water liquid premix, which can comprise water at a level of less than 20%, preferably less than 15%, more preferably less than 10% by weight of the resultant liquid composition.

The present disclosure is directed toward a liquid composition comprising: a) at least one surfactant; and b) at least one polysaccharide structurant. The surfactant can be selected from the group consisting of: anionic surfactant, nonionic surfactant, cationic surfactant, and mixtures thereof. The liquid composition can comprise from 0.5 to 40 wt % of the surfactant. The polysaccharide structurant i), ii), and/or iii) can constitute between 0.1 wt % and 15 wt % of the total liquid composition.

The liquid composition can further comprise at least one enzyme wherein the enzymes are cellulases, endoglucanase with activity towards xyloglucan, or a combination thereof. The liquid composition can further comprise a suspended insoluble material. The liquid composition can further comprise a water-soluble polymer. The water-soluble polymer can be one or more of carboxylate polymers, polyethylene glycol polymers, polyester soil release polymers such as terephthalate polymers, amine polymers, cellulosic polymers, dye transfer inhibition polymers, dye lock polymers such as a condensation oligomer produced by condensation of imidazole and epichlorhydrin, optionally in ratio of 1:4:1, hexamethylenediamine derivative polymers, or a combination thereof. The liquid composition can further comprise water.

The present disclosure is further directed toward a process to manufacture a liquid composition comprising at least one surfactant and a polysaccharide structurant i), ii) and/or iii), the process comprising the steps of: (a) providing a liquid premix comprising the surfactant; (b) providing a structuring premix comprising the polysaccharide structurant i), ii) and/or iii); and (c) incorporating the structuring premix into the liquid premix using high shear mixing. The structuring premix can comprise a surfactant.

The present disclosure is still further directed toward a use of the polysaccharide structurant i), ii) and/or iii) for structuring a surfactant-containing liquid composition.

The present disclosure is still further directed toward a method for treating a substrate by contacting the substrate with a liquid composition comprising: a) at least one surfactant; and b) a polysaccharide, wherein the polysaccharide structurant is i) a colloidal dispersion of poly alpha-1,3-glucan, ii) poly alpha-1,3-glucan fibrids, iii) soy polysaccharide or iv) a combination thereof. The substrate can be a fabric, dish or hard surface.

In certain embodiments, the liquid composition is a gel detergent composition comprising an organic solvent selected from the group consisting of low molecular weight aliphatic or aromatic alcohols, low molecular weight alkylene glycols, low molecular weight alkylene glycol ethers, low molecular weight esters, low molecular weight alkylene amines, low molecular weight alkanolamines, and mixtures thereof.

In another embodiment, the liquid composition is a hard surface cleaning composition, preferably wherein the hard surface cleaning composition impregnates a nonwoven substrate. As used herein "impregnate" means that the hard surface cleaning composition is placed in contact with a nonwoven substrate such that at least a portion of the nonwoven substrate is penetrated by the hard surface cleaning composition, preferably the hard surface cleaning composition saturates the nonwoven substrate.

In another embodiment, the liquid composition may also be utilized in household or car care compositions, for cleaning various surfaces, such as, for example, hard wood, tile, ceramic, plastic, leather, metal, or glass.

In another embodiment, the liquid composition is a household care composition, for example, bathroom cleaners, or carpet shampoos.

In another embodiment, the liquid composition is a dish cleaning composition, for example, liquid hand dishwashing compositions, solid automatic dishwashing compositions, liquid automatic dishwashing compositions, or tab/unit dose forms of automatic dishwashing compositions.

In another embodiment, the liquid composition is a personal care or pet care composition, for example, shampoo composition, hair rinses, mouthwashes, denture cleaners, body wash (e.g., shower gels and foam baths), or liquid or solid soap.

In another embodiment, the liquid composition is one that comes into contact with free hardness and/or requires hardness tolerant surfactant systems, for example, compositions comprising metal cleaners, oil cleaners, corrosion inhibitors, or anti-tarnish aids.

In another embodiment, the liquid composition is an automotive care compositions, for example, car shampoos.

Test Methods

Viscosity was measured by a Brookfield DV3T Rheometer equipped with a recirculating bath to control temperature (20° C.) and a YULA15-E(Z) spindle. The shear rate was increased using a gradient program which increased from 0.01-7.45 s$^{-1}$ and then shear rate was increased by 0.16 s$^{-1}$ every 30 seconds. The shear rate was then increased using a gradient program which increased from 0.01 to 250 s$^{-1}$ and the shear rate was increased by 6.5 s$^{-1}$ every 20 seconds.

Fibrid dimensions were measured using HiRes Fiber Quality Analyzer (OpTest Equipment, Inc., Ontario, Canada) in accordance with TAPPI T271 and ISO 16065.

Canadian Standard Freeness (CSF) was determined in accordance with ISO 5267/2 and TAPPI T227 and reported in ml.

Gurley Air Resistance of papers was measured in accordance with TAPPI T460 and reported in seconds/100 ml.

EXAMPLES

The disclosed invention is further defined in the following Examples. It should be understood that these Examples, while indicating certain preferred aspects of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Preparation of Poly Alpha-1,3-Glucan

U.S. Pat. No. 7,000,000 disclosed a polysaccharide fiber comprising hexose units wherein at least 50% of the hexose units within the polymer were linked via alpha-1,3-glycosidic linkages using a *Streptococcus salivarius* gtfJ enzyme. This enzyme utilizes sucrose as a substrate in a polymerization reaction producing poly alpha-1,3-glucan and fructose as end-products.

A slurry of poly alpha-1,3-glucan was prepared from an aqueous solution (0.5 L) containing *Streptococcus salivarius* gtfJ enzyme (100 unit/L) described in U.S. Patent Appl. Publ. No. 2013/0244288, which is incorporated herein by reference in its entirety, sucrose (100 g/L) obtained from OmniPur Sucrose (EM8550), potassium phosphate buffer (10 mM) obtained from Sigma Aldrich, and FermaSure®, an antimicrobial agent, (100 ppm) obtained from DuPont adjusted to pH 5.5. The resulting enzyme reaction solution was maintained at 20-25° C. for either 24 hours or 4 hours. A slurry was formed since the poly alpha-1,3-glucan synthesized in the reaction was aqueous insoluble. The poly alpha-1,3-glucan solids produced in the reaction were collected using a Buchner funnel fitted with a 325-mesh screen over 40 micrometer filter paper, forming the wet cake which contains about 60-80 wt % of water. The poly alpha-1,3-glucan wet cake can be dispersed in water using an Ika Ultra-Turrax T25 digital disperser, typically operating at 8,000 rpm for 5 min at ambient temperature to make a colloidal dispersion of poly alpha-1,3-glucan. The enzyme reaction solution maintained at 20-25° C. for 24 hours can produce a colloidal dispersion capable of lower viscosity and the enzyme reaction solution maintained at 20-25° C. for 4 hours can produce a colloidal dispersion capable of higher viscosity.

Example 1

Liquid Composition with Poly Alpha-1,3-Glucan

Example 1 is a liquid composition prepared with a colloidal dispersion of alpha-1,3-glucan as the polysaccharide structurant. A liquid premix was prepared by stirring together 15.1 g water, 3.1 g sodium hydroxide as 50 wt % sodium hydroxide in water (available from EMD Chemicals, Gibbstown N.J.), 2.5 g dodecylbenzene sulfonate, an anionic surfactant, (available from Sigma Aldrich, St. Louis, Mo.), 1.4 g citric acid (available from Avantor Performance Materials, Center Valley, Pa.), 1.3 g stearic acid (available from Sigma Aldrich, St. Louis, Mo.) and 1.5 g Tergitol®, a nonionic surfactant, (available from Sigma Aldrich, St. Louis, Mo.). A structuring premix was prepared by stirring together 1.3 g 1,3-propanediol (available from Spectrum Chemicals, New Brunswick, N.J.), 1.9 g Tergitol, a nonionic surfactant, (available from Sigma Aldrich, St. Louis, Mo.) and the polysaccharide structurant used was made using 0.75 g of 24 wt % poly alpha-1,3-glucan wet cake in water. The liquid premix was then added to the structuring premix using an Ultra Turrax high shear mixer operating at 13,500 rpm for 2 min to achieve a homogenous colloidal dispersion of the poly alpha-1,3-glucan. Viscosity data was collected and reported in Table 1.

Example 2

Liquid Composition with Poly Alpha-1,3-Glucan

Example 2 is a liquid composition prepared with external polysaccharide structurant in a similar manner to Example 1 except that 1.27 g of 14.2 wt % poly alpha-1,3-glucan wet cake in water was used as the polysaccharide structurant with higher capable colloidal dispersion. Viscosity data was collected and reported in Table 1.

Comparative Example A

Liquid Composition without External Structurant

Comparative Example A is a liquid composition prepared without a polysaccharide structurant (i.e., no poly alpha-1,3-glucan was used) in a similar manner to Example 1. Viscosity data was collected and reported in Table 1.

TABLE 1

Viscosity Data for Liquid Compositions with Poly Alpha-1,3-Glucan

| | Examples | | |
|---|---|---|---|
| | 1 | 2 | A |
| Viscosity at 1.1 Shear Rate for 24 h s$^{-1}$ | 13,389 | 18,813 | 10,254 |
| Viscosity at 1.1 Shear Rate for 2 wk s$^{-1}$ | 21,864 | 23,050 | 13,135 |

Table 1 shows that liquid compositions made with the colloidal dispersion of poly alpha-1,3-glucan, as the polysaccharide structurant, have higher viscosity than a liquid composition made without the polysaccharide structurant.

Example 3

Liquid Composition with Poly Alpha-1,3-Glucan

Example 3 is a liquid composition prepared with external polysaccharide structurant in a similar manner to Example 1 except that only half as much poly alpha-1,3-glucan wet cake was used. Viscosity data was collected and reported in Table 2.

Example 4

Liquid Composition with Poly Alpha-1,3-Glucan

Example 4 is a liquid composition prepared with external polysaccharide structurant in a similar manner to Example 2 except that only half as much poly alpha-1,3-glucan wet cake was used. Viscosity data was collected and reported in Table 2.

Comparative Example B

Liquid Composition without External Structurant

Comparative Example A is a liquid composition prepared without external polysaccharide structurant in a similar manner to Comparative Example A. Viscosity data was collected and reported in Table 2.

TABLE 2

Viscosity Data for Liquid Compositions with Poly Alpha-1,3-Glucan

| | Examples | | |
|---|---|---|---|
| | 3 | 4 | B |
| Viscosity at 1.03 Shear Rate for 24 h s$^{-1}$ | 5,820 | 9,950 | 4,617 |
| Viscosity at 1.1 Shear Rate for 1 wk s$^{-1}$ | 12,881 | 14,661 | 10,847 |

Table 2 shows that liquid compositions made with poly alpha-1,3-glucan, as an external structurant, have higher viscosity than a liquid composition made without an external structurant.

Preparation of Poly Alpha-1,3-Glucan Wet Cake and Dry Solid

A slurry of poly alpha-1,3-glucan was prepared from an aqueous solution (0.5 L) containing *Streptococcus salivarius* gtfJ enzyme (100 unit/L) described in U.S. Patent Appl. Publ. No. 2013/0244288, which is incorporated herein by reference in its entirety, sucrose (100 g/L) obtained from OmniPur Sucrose (EM8550), potassium phosphate buffer (10 mM) obtained from Sigma Aldrich, and FERMASURE®, an antimicrobial agent, (100 ppm) obtained from DuPont adjusted to pH 5.5. The resulting enzyme reaction solution was maintained at 20-25° C. for 24 hours. A slurry was formed since the poly alpha-1,3-glucan synthesized in the reaction was aqueous insoluble. The poly alpha-1,3-glucan solids produced in the reaction were collected using a Buchner funnel fitted with a 325-mesh screen over 40 micrometer filter paper, forming the wet cake which contained about 60-80 wt % water. The poly alpha-1,3-glucan wet cake was then dried to make the dry poly alpha-1,3-glucan solid.

Examples 5 and 6

Preparation of Poly Alpha-1,3-Glucan Fibrids

Dispersions can be prepared with 0.8 wt % and 2 wt % poly alpha-1,3-glucan, Example 5 and 6, respectively. The dope for Example 5 was prepared from 40 grams of aqueous solution containing 14 wt % poly alpha-1,3-glucan and 4.5 wt % NaOH. The dope was slowly added under high shear to a blender with 200 g pH 2 aqueous sulfuric acid to precipitate the fibrids. The blender contents were filtered to isolate the fibrids. The dope for Example 6 was prepared from 40 grams of aqueous solution containing 14 wt % poly alpha-1,3-glucan and 4.5 wt % NaOH. The dopes was slowly added under high shear to a blender with 200 g pH 10 aqueous sodium hydroxide solution to precipitate the fibrids.

Example 7

Liquid Composition with Poly Alpha-1,3-Glucan Fibrids

Example 7 is a liquid composition prepared in which poly alpha-1,3-glucan fibrids were used as the polysaccharide structurant. A liquid premix was prepared by stirring together 7.4 g water, 3.1 g sodium hydroxide as 50 wt % sodium hydroxide in water (available from EMD Chemicals, Gibbstown N.J.), 2.5 g dodecylbenzene sulfonate, an anionic surfactant, (available from Sigma Aldrich, St. Louis, Mo.), 1.4 g citric acid (available from Avantor Performance Materials, Center Valley, Pa.), 1.3 g stearic acid (available from Sigma Aldrich, St. Louis, Mo.) and 1.5 g TERGITOL®, a nonionic surfactant, (available from Sigma Aldrich, St. Louis, Mo.). A structuring premix was prepared by stirring together 1.3 g 1,3 propanediol (available from Spectrum Chemicals, New Brunswick, N.J.), 1.9 g Tergitol, a nonionic surfactant, (available from Sigma Aldrich, St. Louis, Mo.) and 10.7 g of 0.8 wt % poly alpha-1,3-glucan fibrids in water, as the polysaccharide structurant, in water. The liquid premix was then added to the structuring premix using an Ultra Turrax high shear mixer operating at 13,500 rpm for 2 min to achieve a homogenous liquid composition. Viscosity data was collected and reported in Table 3.

Example 8

Liquid Composition with Poly Alpha-1,3-Glucan Fibrids

Example 8 is a liquid composition prepared with polysaccharide structurant in a similar manner to Example 7 except that twice as much poly alpha-1,3-glucan fibrids was used. Specifically, the polysaccharide structurant was prepared using 9.0 g of 2.0 wt % poly alpha-1,3-glucan fibrids in water. Viscosity data was collected and reported in Table 3.

Comparative Example C

Liquid Composition without External Structurant

Comparative Example C is a liquid composition prepared without external structurant in a similar manner to Example 7 except that no external structurant, poly alpha-1,3-glucan fibrids was added. Viscosity data was collected and reported in Table 3.

TABLE 3

Viscosity Data for Liquid Compositions with Poly Alpha-1,3-Glucan Fibrids

| | Examples | | |
|---|---|---|---|
| | 7 | 8 | C |
| Viscosity at 1.1 Shear Rate for 24 h s$^{-1}$ | 7,542 | 8,518 | 4,617 |
| Viscosity at 1.1 Shear Rate for 2 wk s$^{-1}$ | 14,154 | 13898 | 10,847 |

Table 1 shows that liquid compositions made with poly alpha-1,3-glucan fibrids as the external structurant, have higher viscosity than a liquid composition made without an external structurant.

What is claimed is:

1. A liquid composition comprising:
   (a) at least one surfactant; and
   (b) at least one polysaccharide structurant;
   wherein the polysaccharide structurant is:
      (i) a colloidal dispersion of poly alpha-1,3-glucan;
      (ii) poly alpha-1,3-glucan fibrids; or
      (iii) a combination thereof.

2. The liquid composition of claim 1, wherein the surfactant is selected from the group consisting of: anionic surfactant, nonionic surfactant, cationic surfactant, and mixtures thereof.

3. The liquid composition of claim 1, wherein the liquid composition comprises 0.5wt % to 40 wt % of the surfactant.

4. The liquid composition of claim 1, wherein the liquid composition comprises 0.1 wt % to 15 wt % of the polysaccharide structurant.

5. The liquid composition of claim 1, wherein the liquid composition further comprises at least one enzyme.

6. The liquid composition of claim 1, wherein the liquid composition further comprises a suspended insoluble material.

7. The liquid composition of claim 1, wherein the liquid composition further comprises a water-soluble polymer.

8. The liquid composition of claim 7, wherein the water-soluble polymer is a carboxylate polymer, polyethylene glycol polymer, polyester soil release polymer, amine polymer, cellulosic polymer, dye transfer inhibition polymer, dye lock polymer, hexamethylenediamine derivative polymer, or combination thereof.

9. A process to manufacture a liquid composition comprising at least one surfactant and a polysaccharide structurant, the process comprising the steps of:
   (a) providing a liquid premix comprising the surfactant;
   (b) providing a structuring premix comprising the polysaccharide structurant; and
   (c) incorporating the structuring premix into the liquid premix using high shear mixing, wherein the polysaccharide structurant is:
      i) a colloidal dispersion of poly alpha-1,3-glucan;
      ii) poly alpha-1,3-glucan fibrids; or
      iii) combination thereof.

10. The process of claim 9, wherein the structuring premix comprises a surfactant.

11. A method for treating a substrate by contacting the substrate with a liquid composition according to claim 1.

12. The method of claim 11, wherein the substrate is a fabric, dish, or hard surface.

13. The liquid composition of claim 1, wherein at least 80% of the glycosidic linkages of the poly alpha-1,3-glucan of the colloidal dispersion or the fibrids are alpha-1,3 glycosidic linkages.

14. The liquid composition of claim 1, wherein the polysaccharide structurant is said colloidal dispersion.

15. The liquid composition of claim 1, wherein the polysaccharide structurant is said poly alpha-1,3-glucan fibrids.

16. The liquid composition of claim 5, wherein the enzyme is a cellulase, or an endoglucanase with activity towards xyloglucan.

17. The liquid composition of claim 5, wherein the enzyme is a protease, amylase, mannanase, or pectate lyase.

18. A liquid composition comprising:
(a) at least one surfactant;
(b) water; and
(c) at least one polysaccharide structurant;
wherein the polysaccharide structurant is:
(i) a colloidal dispersion of poly alpha-1,3-glucan;
(ii) poly alpha-1,3-glucan fibrids; or
(iii) a combination thereof.

19. The liquid composition of claim 18, wherein the surfactant is selected from the group consisting of: anionic surfactant, nonionic surfactant, cationic surfactant, and mixtures thereof.

20. The liquid composition of claim 18, wherein the liquid composition further comprises at least one enzyme.

21. The liquid composition of claim 18, wherein the enzyme is a protease, amylase, mannanase, pectate lyase, or cellulase, or an endoglucanase with activity towards xyloglucan.

22. The liquid composition of claim 18, wherein the liquid composition further comprises a suspended insoluble material.

23. The liquid composition of claim 18, wherein the liquid composition further comprises a water-soluble polymer.

24. The liquid composition of claim 23, wherein the water-soluble polymer is a carboxylate polymer, polyethylene glycol polymer, polyester soil release polymer, amine polymer, cellulosic polymer, dye transfer inhibition polymer, dye lock polymer, hexamethylenediamine derivative polymer, or combination thereof.

25. The liquid composition of claim 18, wherein at least 80% of the glycosidic linkages of the poly alpha-1,3-glucan of the colloidal dispersion or the fibrids are alpha- 1,3 glycosidic linkages.

26. The liquid composition of claim 18, wherein the polysaccharide structurant is said colloidal dispersion.

27. The liquid composition of claim 18, wherein the polysaccharide structurant is said poly alpha-1,3-glucan fibrids.

28. A method for treating a substrate by contacting the substrate with a liquid composition according to claim 18.

29. The method of claim 28, wherein the substrate is a fabric, dish, or hard surface.

30. The process of claim 9, wherein the liquid premix and/or the structuring premix further comprise water.

* * * * *

UNITED STATES PATENT AND TRADEMARK OFFICE
CERTIFICATE OF CORRECTION

PATENT NO. : 10,738,266 B2
APPLICATION NO. : 15/572223
DATED : August 11, 2020
INVENTOR(S) : Rakesh Nambiar et al.

It is certified that error appears in the above-identified patent and that said Letters Patent is hereby corrected as shown below:

In the Claims

Column 23 In Claim 21 should read:
21. The liquid composition of claim 20, wherein the enzyme is a protease, amylase, mannanase, pectate lyase, or cellulase, or an endoglucanase with activity towards xyloglucan.

Signed and Sealed this
First Day of October, 2024

Katherine Kelly Vidal
*Director of the United States Patent and Trademark Office*